United States Patent [19]

Chirife

[11] Patent Number: 4,719,921
[45] Date of Patent: Jan. 19, 1988

[54] CARDIAC PACEMAKER ADAPTIVE TO PHYSIOLOGICAL REQUIREMENTS

[76] Inventor: Raul Chirife, Pirovana 137, 1640 Martinez Buenos Aires, Argentina

[21] Appl. No.: 770,205

[22] Filed: Aug. 28, 1985

[51] Int. Cl.[4] .............................................. A61N 1/36
[52] U.S. Cl. ................................ 128/419 PG; 128/703
[58] Field of Search ........................ 128/419 PG, 703

[56] References Cited

U.S. PATENT DOCUMENTS

| | | | |
|---|---|---|---|
| 4,009,721 | 3/1977 | Alcidi | 128/419 PG |
| 4,228,803 | 10/1980 | Rickards | 128/419 PG |
| 4,313,442 | 2/1982 | Knudson et al. | 128/419 PG |
| 4,527,568 | 7/1985 | Richards | 128/419 PG |
| 4,535,774 | 8/1985 | Olson | 128/419 PG |
| 4,556,062 | 12/1985 | Grassi et al. | 128/419 PG |

OTHER PUBLICATIONS

Chirife et al., "Densitography: A New Method for Evaluation of Cardiac Performance at Rest and During Exercise", *Am. Heart J.*, vol. 83, No. 4, Apr. 1972, pp. 493–503.
Martin et al., "Direct Correlation of External Systolic Time Intervals with Internal Indices of Left Ventricular Function in Man", *Circulation*, vol. XLIV, Sep. 1971, pp. 419–431.
Harris et al., "Effects of Adrenergic Receptor Activation and Blockade on the Systolic Preejection Period, Heart Rate, and Arterial Pressure in Man", *J. Clin. Investigation*, vol. 46, No. 11, 1967, pp. 1704–1714.

*Primary Examiner*—William E. Kamm
*Attorney, Agent, or Firm*—Fuller, Puerner & Hohenfeldt

[57] ABSTRACT

A cardiac pacemaker has a pacing pulse generator whose rate is adjusted as a function of the cardiac output requirements of the body that are commensurate with the activity of the individual. The length of the ventricular preejection period (PEP) is governed by body hormones as well as direct nerve action upon the heart in relation to stress. The PEP is determined by marking occurrence of the onset of a natural ECG signal or artificial pacing pulse, whichever is first to occur in a heart cycle, and detecting left or right ventricular ejection by a pressure or flow pulse in the arterial system or a volume change in the right ventricle. The length of time between the onset of a natural or artificial stimulus and onset of ventricular ejection is the PEP. An electric signal that depends on the PEP is used to regulate the pulse generator rate and escape mechanisms in any of the conventional pacing modes including the AAI, VVI, DVI, VDD and DDD modes.

5 Claims, 3 Drawing Figures

CARDIAC PACEMAKER ADAPTIVE TO PHYSIOLOGICAL REQUIREMENTS

BACKGROUND OF THE INVENTION

The invention disclosed herein is a cardiac pacemaker that responds to varying physiological or metabolic requirements of the body by automatically adjusting the stimulus or pacing rate and, hence, the blood pumping rate of an abnormal heart to the same extent that the body would naturally adjust the rate of a normal heart for equivalent physiological requirements.

The body maintains a hormone level in the blood that is related to the prevailing amount of physical activity and emotional stress. When a person increases physical activity voluntarily or is subjected to a challenge that results in stress, the level of the activating hormones increases. By a complex but short duration chain of events, the heart responds to the hormone level or direct nerve action by beating at a higher rate so as to pump a sufficient volume of blood for coping with the increased demand. The converse of the foregoing occurs when the person goes from a physically active state to a resting state.

Normally, changes in physical activity alter the rate of the nerve impulses to the sino-atrial (SA) node of the heart. This node depolarizes in response to receiving said nerve impulses and causes an electric signal to be propagated over the atrium which causes it to contract and discharge blood into the ventricles. The atrial signal is conducted to the atrio-ventricular (AV) node which, after a short delay, causes a depolarizing signal to be propagated over the ventricles, thus causing the ventricles to contract and to discharge blood to the aorta and pulmonary artery. Simultaneously with increased rate, ventricular contractility is enhanced.

The electrical system of the heart is subject to various kinds of failures. In some cases, the natural or intrinsic electric signals of the atrium occur at a rate in correspondence with hormone levels and physiological requirements but the signals are not propagated to or through the Purkinje fibers which conduct the signals from the AV node to the ventricles. Hence, the ventricles do not depolarize immediately in which case ventricular contraction is delayed and falls out of synchronism with the atrium. The ventricles have an escape capability which is to say that even though they do not receive a conducted signal they will depolarize by themselves eventually and cause ventricular contraction. This slow ventricular rate results in an inadequate supply of blood to the organs which reduces patient's work capacity and can result in a patient fainting, especially if an attempt is made to increase activity.

In some individuals, the defect in the electrical system of the heart is such that the heart generates natural or intrinsic stimulus signals some of the time but fails to generate them at other times. Pacemakers that provide artificial electric stimuli on demand are usually implanted in the subject when ventricular contractions are missed or unduly delayed periodically. The latest demand pacemaker designs can be programmed from outside of the body to operate in any of several modes. For instance, a pacemaker may be controlled to pace the atrium only, or to pace ventricles only, or to pace the heart chambers synchronously, first the atrium, then delay, then ventricle stimulation. In demand pacemakers, the pacing rate is set sufficiently high to assure that enough blood will be pumped to permit a limited amount of physical activity above a resting state.

In some cases the pacemaker is operated in the atrial synchronous mode. The atrial signal is detected and used to adjust the artificial stimulus or pacing rate of the pacing pulse generator in the ventricle to match physiological requirements. This is based on the assumption that the nerve impulses to the SA node increase and decrease faithfully in response to changes in demand. There is coordination between the natural atrial signal timing and variable physiological requirements, but the signals are difficult to detect with accuracy. In some subjects, the atrial signal is not synchronized with the ventricular signal. U.S. Pat. No. 4,313,442 exhibits one attempt to solve this problem.

It is known that with a healthy heart, the QT interval in the natural ECG signal changes in relation to physiological demand, that is, the QT interval shortens as exercise is increased. U.S Pat. No. 4,228,803 uses this phenomenon to adjust the artificial stimulus pulse rate in relation to physiological requirements. The interval between the QRS complex in the ECG waveform and the T-wave is measured for every heart beat. As the T-wave interval shortens, the rate of the stimulus pulse generator is increased and as the interval lengthens, the pulse rate is decreased. This has not completely solved the problem of coordinating pacing rate with physiological demand because the QT interval is not wholly independent of pacing rate. When physical activity of the person is increased voluntarily, a natural contribution to shortening the T-wave interval occurs. The pacemaker senses this as a requirement for increasing the artificial stimulus rate. This shortens the interval further. Thus, there is a positive feedback and the pacemaker can go into a needless cycle of self-acceleration. Pacemakers of this type can increase the stimulus pulse rate even though physical activity has not increased.

Other attempts have been made to match stimulus pulse rate with physiological needs. One example is given in U.S. Pat. No. 4,009,721 which is based on recognition that the pH level of the blood is a function of physical activity. The pH is detected and converted to a signal useful for adjusting the rate of the stimulus pulse generator. However, there is doubt as to whether a system can respond to physiological requirements on a beat-to-beat basis.

A deficiency that exists in all prior art pacemakers which attempt to respond to physiological requirements is that they do not change stimulus rate in response to emotional stress or simply a challenge to the body without increase in physical activity as nature provides in a healthy individual with a normal heart.

SUMMARY OF THE INVENTION

In accordance with the present invention, regulation of the stimulus pulse rate of an electronic pacemaker is based upon the recognition that in subjects which have either normal or abnormal cardiac electrical systems, the ventricular preejection period (PEP) and the isovolumic contraction time (IVCT) within said period vary naturally and faithfully in direct correspondence with physiological requirements of the body.

As is well known, during systole, that is, during ventricular contraction, blood pressure in the aorta and pulmonary artery rises until their valves close after which the pressure pulse declines to a rather steady state during diastole. A cardiac cycle begins with initiation of the QRS complex in the electrocardiogram (ECG) waveform. It takes a certain amount of time-for an intrinsic heart stimulus signal or an artificial pacing pulse to propagate and to effect depolarization of the ventricular tissue cells so there is a short delay before ventricular contraction starts. The point in time at which contract,ion starts coincides with the beginning of the isovolumic contraction time (IVCT). During IVCT there is no ejection of blood from the ventricles. Finally, the pressure in the ventricles exceeds the residual back pressure in the aorta or pulmonary artery and ventricular ejection begins. The time elapsed between the beginning of the QRS complex or the artificial pacing pulse and the onset of ventricular contraction is defined as the preejection period (PEP).

When the body is subjected to any physical or emotional stress and when physical activity is voluntarily increased, there is an increased sympathetic nerve action upon the heart and catecholamines release by the adrenal glands into the blood stream. This enhances metabolic activity in the musculature sufficiently to effect the necessary response to the stress or increased activity by increasing contractility of the heart and its rate. It has been demonstrated that the IVCT varies with the cathecolamine levels and decreases in length as physical activity increases and increases as physical activity is decreased. A study and confirmation of this phenomenon is presented in Harris, W. S., Schoenfeld, CD, and Weissler, A. M.: "Effects Of Adrenergic Receptor Activation and Blockade on the Systolic Preejection Period, Heart Rate, and Atrial Pressure in Man". *The Journal of Clinical Investigation* Vol. 46 No. 11, 1967. Tests conducted in connection with establishing the hypothesis of the present invention confirm the value and consistent relationship of IVCT and PEP with changes in stress and activity.

In accordance with the present invention, an artificial electronic pacemaker is adapted to alter its stimulus pulse rate in response to body controlled variations in PEP which parallel the normal atrial rate variations from the same stimuli.

The primary objective of the invention is to provide an artificial pacemaker device with the capability of altering its stimulus pulse rate and, hence, control the blood volume pumped, in faithful conformity with metabolic requirements of the body just as a healthy body and heart respond to said requirements.

Another objective is to achieve, for the first time in pacemaker technology, alteration of the stimulus pulse rate in response to the body simply being subjected to emotional and other non-dynamic challenges such as hot, cold, fear or isometric stress analogously to the way a normal body functions.

Another objective is to provide a device for controlling stimulus pulse rate that can be incorporated in most, if not all, modern pacemaker designs.

Briefly stated, the new pacemaker system comprises a first device that senses the beginning of each natural QRS waveform in the ECG signal. If there is no natural QRS signal within an escape interval to cause the heart to beat, then the artificial stimulus pulse provided as a substitute by the pacemaker is sensed. In either case, the sensed signal corresponds to the time the heart is being signalled to initiate ventricular contraction. After a delay extending to the beginning of the IVCT, the ventricles begin to contract, but no blood is being ejected as yet. A second sensor is used to detect the moment the blood pressure in the contracting ventricle equals the static diastolic pressure in the aorta or pulmonary artery or when blood begins to flow in said vessels or other arteries. The time corresponds to the onset of ventricular ejection and constitutes the end of the PEP. Thus, with the beginning of the QRS complex or signal being sensed and the subsequent signal indicative of ventricular ejection being sensed, the time of ejection relative to the beginning of the QRS signal can be measured and the measured interval represents the PEP. A signal corresponding to the variable PEP and, hence, to variable physiological requirements is used to adjust the pacemaker stimulus pulse rate and escape interval.

As previously indicated, it is the IVCT that is caused to vary naturally in response to the cathecolamines that are released into the blood as well as to direct sympathetic nerve activity when physiological requirements increase. Measurements show, however, that the delay between onset of the QRS complex and the onset of IVCT is constant for each patient and the delay between an artificial stimulus pulse and onset of the IVCT is also constant for each patient. It is difficult to sense the onset of the IVCT on a continuing basis outside of the laboratory, that is, in a mobile patient. However, if the PEP is measured as is the case here, it will vary faithfully in proportion to physiological requirements and will be wholly independent of the largely uncertain changes in the QT interval as activity changes.

That there is direct correlation between IVCT, PEP and ventricular ejection is shown by Martin, C. E., Shaver, J. A., Thompson, M. E., Reddy, P. S. and Leonard, J. J.: "Direct Correlation of External Systolic Time Intervals With Internal Indices of Left Ventricular Function In Man." *Circulation*, Vol. XLIV, September 1971. That left ventricular ejection time (LVET) can be determined by sensing pressure or flow in a variety of blood vessels besides the aorta with various types of sensing means is demonstrated by Chirife, R., Pigott, V. M., Spodick, D. H.: "Measurement of the Left Ventricular Ejection Time By Digital Plethysmography." *American Heart Journal* Vol. 82 no. 2 pp. 222-227, August 1971. Also by the same researchers: "Ejection Time By Ear Densitogram and Its Derivative." *Circulation* Vol. XLVIII, August 1973.

A more detailed explanation of an illustrative embodiment of the invention will now be set forth in reference to the drawing.

DESCRIPTION OF A PREFERRED EMBODIMENT

Figure 1:
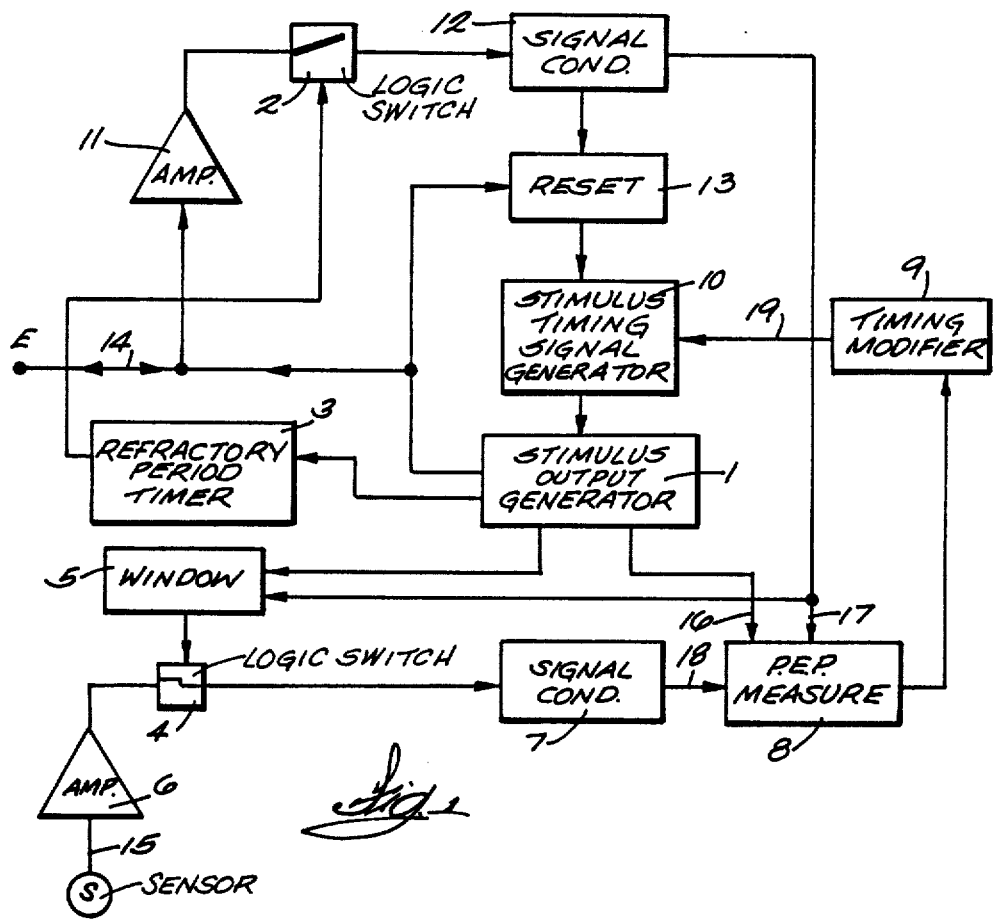
FIG. 1 is a block diagram for illustrating one of several ways that the invention can be implemented in a pacemaker.

The simplified block diagram of a pacemaker in FIG. 1 depicts one example of how the concept of controlling stimulus rate in response to variations in the pre-ejection period (PEP) can be implemented. As usual, the pacemaker is connected to the heart by means of a conductive lead 14 which terminates in an electrode E that contacts the heart. Lead 14 is used to conduct artificial stimulus pulses from the pacemaker to the heart and to pick up natural or intrinsic electric signals on the heart and conduct them to the pacemaker. It is the onset of the QRS signal that is of special interest insofar as the invention is concerned.

In accordance with the invention, means are provided for regulating the stimulus pulse rate in response to variations in the isovolumic contraction time (IVCT) determined by measuring the more easily measurable PEP which is linearly related to the IVCT. The onset of ventricular ejection during each heartbeat is a marker for the end of the PEP. The end of the PEP is determined by sensing the abrupt increase in arterial blood flow that occurs at the onset of ventricular ejection from either ventricle. A blood flow sensor is symbolized in FIG. 1 by an encircled S. Several known types of sensors are adaptable to use with body implantable pacemakers for the purposes of the invention. As one example, a sensor in the form of a photoelectric transducer may be used as described by Chirife and Spodick (Amer. Heart J. 83:493, 1972). Sensors that sense, coincident with ejection, impedance changes in the right ventricle or impedance changes in tissue proximate to arterial vessels anywhere in the body are also suitable. A right ventricular volume detector of the type described by Salo et al (PACE 7:1267, 1984) is suitable too. In general, any implantable device that produces an electric signal in response to the abrupt change in arterial flow or ventricular volume that coincides with ventricular ejection may be used.

The pacemaker in FIG. 1 is a demand type which is characterized by providing an artificial stimulus to the heart by way of lead 14 and electrode E if the natural or intrinsic QRS signal is missing or unduly delayed beyond the escape interval of the pacemaker in any heartbeat cycle. Production of a stimulus by stimulus pulse output generator 1 causes a logic switch 2 to open and remain open during a period determined by a refractory period timer 3. This is a conventional feature in demand pacemakers and assures that the pacemaker will be insensitive to signals such as the evoked QRS or T wave which would adversely affect functioning of the circuit.

In each heartbeat cycle sensor S produces a signal indicative of the onset of ventricular ejection and, hence, the end of the PEP. The starting point of the PEP coincides with the occurrence of the onset of the intrinsic QRS signal or the stimulus pulse whichever occurs first in a heart cycle. The signal from sensor S is supplied by way of a lead 15 to an amplifier 6 in the implanted unit and through a logic switch 4. The output from amplifier 6 is conducted to a signal conditioning circuit 7 which uses bandpass filters and other components, not shown, to discriminate against electrical and motion artifacts in a manner known to pacemaker circuit designers.

The PEP measuring circuit 8 has an input 16 for a signal corresponding to the stimulus pulse, if any, and an input 17 for any detected intrinsic QRS onset signal and an input 18 for the signal indicative of ventricular ejection and the end of the PEP. Thus, the measuring circuit has the information it needs for producing a signal whose value represents the duration of the PEP.

The stimulus timing signal generator 10 controls the rate of the stimulus pulse output generator 1. Generator 10 may be implemented with analog circuitry or digital logic circuitry. Basically, generator 10 generates a signal whose value increases in respect to time and which is reset to a predetermined value such as 0 concurrently with occurrence of each natural or artificial stimulus signal. In a digital implementation of generator 10, clock pulses may be counted to determine the elapsed time since the last heart stimulus and to set the time for the next one as governed by the measured PEP. When physiological demand is low as when the body is at rest, the PEP is longest and the timing signal generator 10 triggers the stimulus pulse generator 1 at the lowest rate. The escape interval or longest time permissible between heartbeats is indicated as having been reached when the number of clock pulses counted since reset exceeds a programmable predetermined number in which case the timing signal generator 10 triggers the stimulus pulse generator 1.

As physical or emotional activity increases, the PEP becomes increasingly shorter and the PEP measuring circuit 8 output signal is translated by a timing modifier circuit 9 into a signal that is sent to timing signal generator 10 by way of line 19. This signal controls the timing signal generator 10 to increase the stimulus pulse rate commensurate with the current level of physical activity. The opposite occurs when the PEP increases as a result of a decline in physical activity or emotional arousal.

In an analog signal circuit implementation of the pacemaker, generator 10 is a ramp signal generator and the slope of the ramp is set with a PEP signal responsive modifier 9 that changes the slope of the ramp as a function of the PEP measured in circuit 8. Again, the relationship between the measured PEP and the slope of the timing ramp generator is externally programmable through modifier circuit 9. A modification in the ramp slope causes the escape interval of the pacemaker to be changed, which in the absence of natural or spontaneous QRS signals will result in a modified pacing rate.

In either the digital or analog circuit implementations of the invention, the stimulus timing signal generator 10 sets an escape interval appropriate to current physiological demand which corresponds to the duration of the measured PEP.

Every time a natural QRS signal is detected by electrode E outside of the refractory period so switch 2 is closed, the signal is amplified by amplifier 11 and conditioned by conditioner 12 so it will cause reset circuit 13 to reset the stimulus timing signal generator 10 to thereby initiate a new cycle. Any detected natural QRS signal or artificial pacing stimulus, whichever occurs first, will activate a window circuit 5 after a programmable delay. Logic switch 4 closes in response to a window interval being started. The use of a programmable delay accounts for the difference among individuals in the elapsed time between occurrence of the natural or artificial stimulus and the start of ventricular ejection. The stimulus signal timing generator 10 will thus be updated by the PEP measurement either from the detected spontaneous QRS signal or the pacing stimulus to the onset of ejection.

Figure 2:
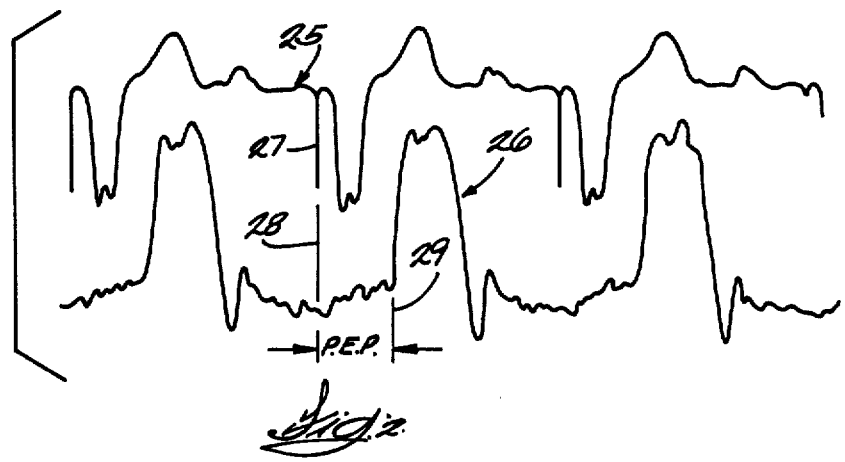
FIG. 2 depicts some waveforms which are useful for explaining the invention.

Attention is now invited to FIG. 2 which shows an ECG waveform 25 and a waveform 26 obtained by densitometry measurement concurrently with the ECG. A typical PEP is marked off. The PEP begins when the heart is stimulated to beat by a pacing pulse. The heart stimulus pacing pulse or the intrinsic pacing pulse, whichever is first to occur in a heart cycle, is detected to mark the start of the PEP. One typical artificial stimulus pulse to which attention is directed is marked 27. In reality, the pace pulses coincide with the onset of the evoked QRS signal. In any event, one may see that the electric signal is applied to the heart for artificial stimulation at a point marked 28 on the pulse waveform 26. There is some delay after the pacing pulse 27 occurs before the heart begins to contract but the delay is constant in any given patient. For a period after the ventricle begins to contract, there is no left ventricular ejection to the aorta. This is so because there is a back pressure in the aorta from the preceding heart beats which must be exceeded before there is ejection under the influence of the contracting left ventricle. The moment of ejection by either ventricle marks the end of the PEP. The measured time between occurrence of the pace signal and ventricular ejection varies in accordance with physical and emotional activity of the body. In other words, the PEP shortens as body activity increases and lengthens as body activity decreases. This is true whether the patient is being artificially stimulated or naturally stimulated for any given heartbeat. It is the cathecolamines and the direct sympathetic nerve action upon the heart that have the effect of varying the PEP when physiological demand for blood increases. In accordance with the present invention, the PEP is measured instead of the IVCT and since it depends on a delay time following the stimulus pulse plus the IVCT, the IVCT in effect, can be calculated by measuring the PEP. This is evident from the waveforms taken from a patient depicted in FIG. 2. All one has to do, in accordance with the invention, is detect the Q-wave or pacing stimulus at point 28, for instance, and the beginning of left ventricular ejection such as at point 29 and a signal proportional to IVCT is obtained. Detecting right ventricular ejection provides the same result.

Figure 3:
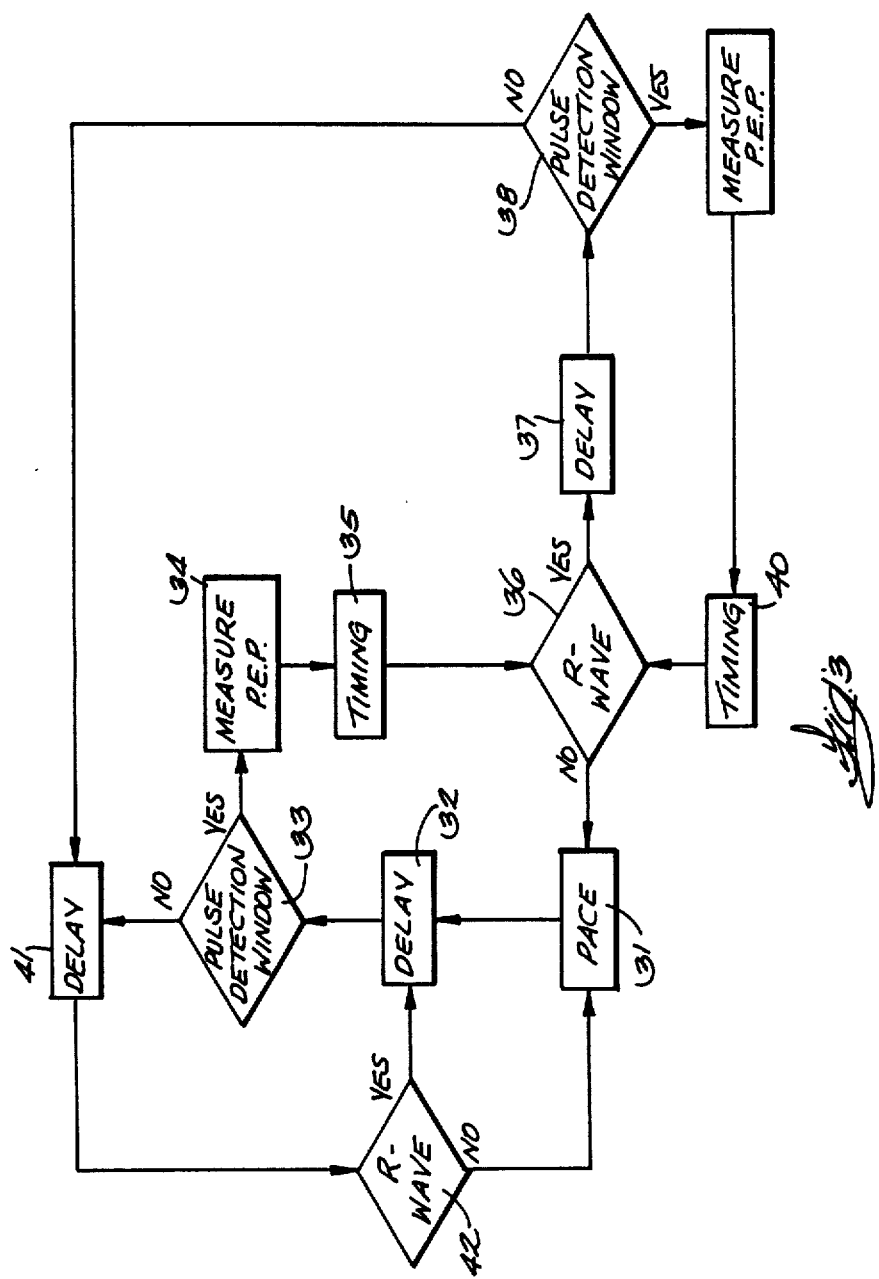
FIG. 3 shows the functional flow chart of the automatic pacemaker described herein.

FIG. 3 is a flow diagram defining the operational sequences of a pacemaker using the new feature of adjusting rate in response to variations in the length of the PEP. Measurement of the length of the PEP as an indicator of the IVCT for every heartbeat permits the adjustment of the timing controls for the stimulus pulse generator in accordance with the demands of the body for blood flow. Starting with a pacing stimulus 31, a measurement window begins after a programmable delay 32 which will differ among individual patients. During this window, a blood pulse wave or ventricular ejection 33 may be detected by the particular previously mentioned sensing device that is used to indicate ventricular ejection. If, (yes) a pulse wave or ejection is detected, the length of the PEP is measured 34 and the timing circuitry 35 of the pacemaker is adjusted; that is, the stimulus pulse rate and escape interval duration are adjusted. During this alert period, either a normally conducted or ectopic spontaneous QRS (R-wave) may occur. If, (no) an R-wave 36 is not detected, a new pacing stimulus 31 is delivered to the heart prior to the end or at the end of an escape interval. If (yes) a QRS or R-wave 36 of said characteristics is present, a new delay 37 is created, followed by a blood pulse detection window 38. If a pulse is detected and PEP measured 39, similar to the above, the timing 40 will again be set, with which the cycle may close with the detection of a patient's R-wave 36 or a pacing stimulus 31. If, on the other hand, following a pacing stimulus 31, no pulse 33 is detected, the stimulus timing will not be modified and the pacemaker will operate in an R-wave 42 demand mode at its preset lower rate. Delay 41 constitutes the alert period for R-wave sensing.

With the invention, anything that would bring about an acceleration of a normal heart will increase the artificial stimulus pulse rate. It has been observed that, besides physical activity, psychological events such as a pleasant or an unpleasant surprise caused the PEP to decrease with the result that the pace pulse rate is increased. The new device is sensitive and can completely restore heart function to normalcy. In healthy individuals the carotid sinuses detect pressure in the arteries. Once pressure is increased in the carotid sinus there is another mechanism which inhibits the heart or slows it down normally by a very small amount in a normal person mediated by the vagus nerve or parasympathetic system. Particularly in elderly patients who have a diseased, hypersensitive carotid sinus and a prevailing high blood pressure or calcification of the carotid artery, the carotid sinuses respond to the mechanical stimuli by slowing down the heart beat too much in which case the patient can faint. The carotid sinuses, of course, provide the signals to the brain and nerve circuits to change the heart rate by nerve action on the SA node. Fortunately, the new system is insensitive to vagal stimulation because the new device does not respond like a normal atrium in this particular case. The new pacemaker system controls the rate in correspondence with PEP (sympathetic action), so carotid pressure will not affect the pacing rate. Said pacing rate would be that existing prior to the time of carotid stimulation and would correspond to the demands of the body for blood at the prevailing level of activity.

I claim:

1. A demand cardiac pacemaker including an adjustable rate artificial stimulus pulse generator having output means for being coupled to a patient's heart to deliver artificial stimulus pulses to said heart, means for detecting the start of ventricular ejection during each heart cycle, means for sensing during each heart cycle an intrinsic heart stimulus signal or an artificial stimulus pulse whichever is first to occur during each heart cycle, said sensed signal or pulse coinciding with the start of the preejection period during said cycle, means for measuring in each heart cycle the length of the PEP constituting the time between occurrence of the intrinsic stimulus signal or stimulus pulse that is sensed by said sensing means and occurrence of ventricular ejection, the length of said PEP being a function of the physiological demand of the patient, means for producing a signal that is a function of the length of said PEP, and means responding to said last named signal by adjusting the rate of said stimulus pulse generator.

2. A cardiac pacemaker comprising:

stimulus pulse generator means for applying artificial stimulus pulse signals to the heart and having an adjustable pulse repetition rate, means for detecting in the heart in each heart cycle the onset of a natural heart stimulus signal or an artificial stimulus pulse signal, whichever occurs first, detection of said signal coinciding with the start of the ventricular preejection period (PEP), means for sensing in said cycle the occurrence of the onset of ventricular ejection, which onset corresponds to the end of said PEP, means for measuring in each heart cycle the length of the PEP constituting the time between occurrence of the stimulus signal that is sensed by said sensing means and occurrence of the onset of ventricular ejection, and means coupled to said pulse generator and responding to the length of said PEP by adjusting the pulse rate of said generator as a function of the length of the PEP.

3. The pacemaker as in claim 2 wherein the onset of said natural signal sensed is the onset of the natural QRS complex.

4. A cardiac pacemaker adaptive to physiological requirements including an adjustable rate pulse generator,
- means for delivering artificial stimulus pulses from said generator to the heart,
- means for sensing in each heart cycle the onset of a natural stimulus of the heart or an artificial stimulus, whichever is first to occur, sensing of said stimulus coinciding with the start of the preejection period (PEP),
- means for sensing the start of ejection of a heart chamber corresponding to the end of the PEP,
- means for measuring the length of time between said start of the PEP and the end of the PEP, and
- means for adjusting the rate of said pulse generator inversely with the length of the PEP.

5. A cardiac pacemaker adapted to respond to current physiological requirements of a patient being paced, comprising:
- adjustable rate pulse generator means having output means for coupling stimulus pulses to the heart,
- first sensing means for sensing in each heart cycle the occurrence of the onset of the QRS complex in the intrinsic heart electrical activity or an artificial pacing pulse, whichever is first to occur in the cycle, sensing of either onset of the QRS complex or the artificial stimulus pulse marking the start of a ventricular preejection period (PEP) whose length varies with said current physiological requirements and during which pressure in the ventricles increases but blood is not ejected therefrom,
- second sensing means for sensing the abrupt increase in blood flow in the arterial system resulting from ventricular ejection, which increase marks the end of the PEP,
- means for measuring the length of time between said start and said end of the PEP to yield a value representative of the length of the PEP,
- means for producing a control signal which is a function of the said value representing the length of the PEP for said signal to control the rate of said pulse generator means,
- means for adjusting the escape interval of said pacemaker in response to an extrasystole having occurred if said extrasystole produces said abrupt increase from which to measure the end of the PEP initiated by said extrasystole, and
- means for adjusting the escape interval in case of failure to detect the end point of the measurement of the PEP initiated by a natural intrinsic ECG waveform or an artificial pacing stimulus.

* * * * *

UNITED STATES PATENT AND TRADEMARK OFFICE
CERTIFICATE OF CORRECTION

PATENT NO. : 4,719,921
DATED : January 19, 1988
INVENTOR(S) : Raul Chirife

It is certified that error appears in the above—identified patent and that said Letters Patent is hereby corrected as shown below:

Claim 1, Column 8, Line 38:

Before "during" insert ---(PEP)---.

Signed and Sealed this

Fourteenth Day of June, 1988

Attest:

DONALD J. QUIGG

*Attesting Officer*       *Commissioner of Patents and Trademarks*